US012678500B2

(12) United States Patent　　(10) Patent No.:　US 12,678,500 B2
Arrington　　(45) Date of Patent:　Jul. 14, 2026

(54) PATHOGEN DESTRUCTION SYSTEM AND METHOD USING MAGNETIC MARKERS

(71) Applicant: Abron Arrington, Denver, CO (US)

(72) Inventor: Abron Arrington, Denver, CO (US)

( * ) Notice: Subject to any disclaimer, the term of this patent is extended or adjusted under 35 U.S.C. 154(b) by 1036 days.

(21) Appl. No.: 17/839,940

(22) Filed: Jun. 14, 2022

(65) Prior Publication Data

US 2022/0409728 A1　　Dec. 29, 2022

Related U.S. Application Data

(60) Provisional application No. 63/215,195, filed on Jun. 25, 2021.

(51) Int. Cl.
　　*A61K 41/00*　　(2020.01)
(52) U.S. Cl.
　　CPC ................................ *A61K 41/0023* (2013.01)
(58) Field of Classification Search
　　None
　　See application file for complete search history.

(56) References Cited

U.S. PATENT DOCUMENTS

| 2011/0077580 | A1* | 3/2011 | Rofougaran | ........ | A61M 31/002 |
| | | | | | 604/20 |
| 2011/0105825 | A1 | 5/2011 | Nayfach-Battilana | | |
| 2014/0378818 | A1* | 12/2014 | Drake | .................... | A61B 18/04 |
| | | | | | 600/414 |

FOREIGN PATENT DOCUMENTS

| AT | 508394 A1 | 1/2011 |
| EP | 1797956 A1 | 6/2007 |

OTHER PUBLICATIONS

Mayer, Robert—AT 508394 A1, Jan. 15, 2011—English translation from Google Patents, pp. 1-2 (Year: 2011).*
A. F. Junka et al., "Application of Rotating Magnetic Fields Increase the Activity of Antimicrobials Against Wound Biofilm Pathogens", Scientific Reports, vol. 8, No. 1, Jan. 9, 2018.
PCT/US2021/062405—International Search Report, dated Mar. 30, 2022.
PCT/US2021/062405—Written Opinion, dated Mar. 30, 2022.

* cited by examiner

*Primary Examiner* — Aradhana Sasan
(74) *Attorney, Agent, or Firm* — Devlin Law Firm LLC

(57)　　　ABSTRACT

A cell destruction method includes providing an anionic biomarker that comprises a magnetic material such as an iron or an iron compound. The anionic biomarker is introduced into an organism having pathogen cells with a negative charge. The anionic biomarkers are attracted to the negative charges of the pathogen and couple thereto. The anionic biomarker may also have a coupler portion that further aids in the anionic biomarker coupling to and being bound to the pathogen cell and/or cell wall. An electric field may be produced to cause the anionic biomarkers and/or the negative charges of the pathogen cell to polarize on or along the pathogen cell. A magnetic field is directed to cause the anionic biomarker, or magnetic material thereof to move and damage the cell. The magnetic field may be an alternating magnetic field that causes the magnetic material to oscillate and damage the cell wall.

11 Claims, 4 Drawing Sheets

PATHOGEN DESTRUCTION SYSTEM AND METHOD USING MAGNETIC MARKERS

CROSS REFERENCE TO RELATED APPLICATIONS

This application claims the benefit of priority to U.S. provisional patent application No. 63/215,195 filed on Jun. 25, 2021; the entirety of which is hereby incorporated by reference herein.

BACKGROUND OF THE INVENTION

Field of the Invention

The invention relates to the use of magnetic biomarkers coupled with pathogens and destruction of the pathogens through agitation of the biomarkers via an alternating magnetic field.

Background

Pathogens are becoming harder to treat with antibiotics due to antibiotic resistant strains. Antibiotic development is on a decline as a result of the diminishing effectiveness. There exists a need for a treatment method to destroy pathogens that does not rely on antibiotics, that is safe and effective for a wide range of pathogens.

SUMMARY OF THE INVENTION

The invention is directed to the use of magnetic biomarkers coupled with pathogens and destruction of the pathogens through agitation of the biomarkers via an alternating magnetic field.

A pathogen, as used herein, is defined as bacterium, virus, or other microorganism that can cause disease.

An exemplary pathogen cell destruction method includes providing an anionic biomarker that comprises a magnetic material or a magnetic material associated or coupled thereto, such as an iron or an iron compound. The anionic biomarker is introduced into an organism having pathogen cells with a negative charge. The anionic biomarkers are attracted to the negative charges of the pathogen and couple thereto due to the electro-potential differences. The anionic biomarker may also have a coupler portion that further aids in the anionic biomarker coupling to and being bound to the pathogen cell and/or cell wall. An electric field may be produced to cause the anionic biomarkers and/or the negative charges of the pathogen cell to polarize on or along the pathogen cell. A magnetic field is directed to cause the anionic biomarker, or magnetic material thereof to move and damage the cell. The magnetic field may be an alternating magnetic field that causes the magnetic material to oscillate and damage the cell wall.

The magnetic field and the electric field may be produced at the same time or the electric field may be applied prior to the magnetic field.

An anionic biomarker may include any suitable biomarker from the FDA list of qualified biomarkers as of Jun. 18, 2021, including, but not limited to, Albumin, β2-Microglobulin, Clusterin, Cystatin C, KIM-1, Total Protein, and Trefoil factor-3, Clusterin, Renal Papillary Antigen (RPA-1), Cardiac troponins T (cTnT) and I (cTnI), Galactomannan, Fibrinogen, Total Kidney Volume (TKV), clusterin (CLU), Cystatin-C (CysC), Kidney Injury Molecule-1 (KIM-1), N-acetyl-beta-D-glucosaminidase (NAG), Neutrophil Gelatinase-Associated Lipocalin (NGAL), and osteopontin (OPN), Plasmodium 18S rRNA/rDNA, and proteins and may have a coupler portion that has a chemical composition and/or structure to mimic a cell or molecule that the pathogen has a propensity to bond to. An anionic biomarker may include positively charged molecules, cytokines, dyes for dying bacteria, chitosan, dyes for imaging, such as CAT scan imaging.

A magnetic material that is associated or coupled with the anionic biomarker may include iron, such as iron oxide or nanoparticle of iron, such as iron oxide nanoparticles. Other ferromagnetic metals include nickel, cobalt, gadolinium, dysprosium and alloys such as steel that also contain specific ferromagnetic metals such as iron or nickel, which may be included as a compound, such as an oxide and/or a nanoparticle. Nanoparticles may be less than a micron in size and may be on the order of tens of nanometers (10 to 90 nm) to hundreds of nanometer (100 to 900 nm), such as from 10 to 500 nm, for example, or less than 750 nm, or less than about 500 nm, or even less than about 250 nm and any range between and including the nanoparticle sizes provided.

The method described herein, may be used for destroying other cells, such as cancer cells, or malignant tissue, wherein a marker is configured to be associated the cell and the marker has a magnetic material coupled thereto that can be moved or oscillated via a magnetic field. The magnetic material may be coupled with the marker initially or subsequent to the markers associating with and being configured in or around the cell or tissue.

In some embodiments, a non-oscillating magnetic field may be used to draw a magnetic material associated with a biomarker through at least a portion of a cell, such as through a portion or completely through the cell wall to destroy the cell. This method may be well suited when the biomarker and/or the magnetic material is absorbed into the cell, especially when the magnetic material is drawn into or through the cell wall.

The Aggressive Trauma Induced Alternating Magnetism system relies upon three components.

1. Two electrodes that are placed in or on the body area to be treated to provide an electric current in order to polarize the cells, molecules and/or pathogens within the body while also inducing a magnetic field.
2. Exogenous biomarkers specifically designed to target and mark specific cells, molecules and/or pathogens; and
3. A second magnet outside the body that provides a stronger magnetic field around the entire body or area of the body to be treated.

Once tagged with biomarkers and polarized by the electric current, the secondary alternating magnetic field outside the body will rapidly and repeatedly depolarize the cells and their respective biomarkers resulting in damage to the targeted cells, tissue and or pathogens.

The method provides a means to tag, or attach nontoxic biomarkers, as described herein to various bacterial, viral and oncological cells and cell structures. A pathogen cell, as used herein, may include a malignant cell, bacteria, viral, or oncological cell or portion thereof. A malignant cell may a carcinogenic pathogens such as HPV, HTLV-1, EBV, MCPyV and KSVH.

The method provides a means to polarize cells and cell structures in-vivo and to alternate the polarity of a magnetic field rapidly to destroy them.

The method provides a means to rapidly polarize and depolarize bacteria, and virus' in-vivo with the use of magnetic fields to remove flagella and surface antigens thereby making it impossible for them to attach and infect hosts.

The exemplary pathogen destruction method may work and take microbial treatment and other treatments as well in a new direction.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
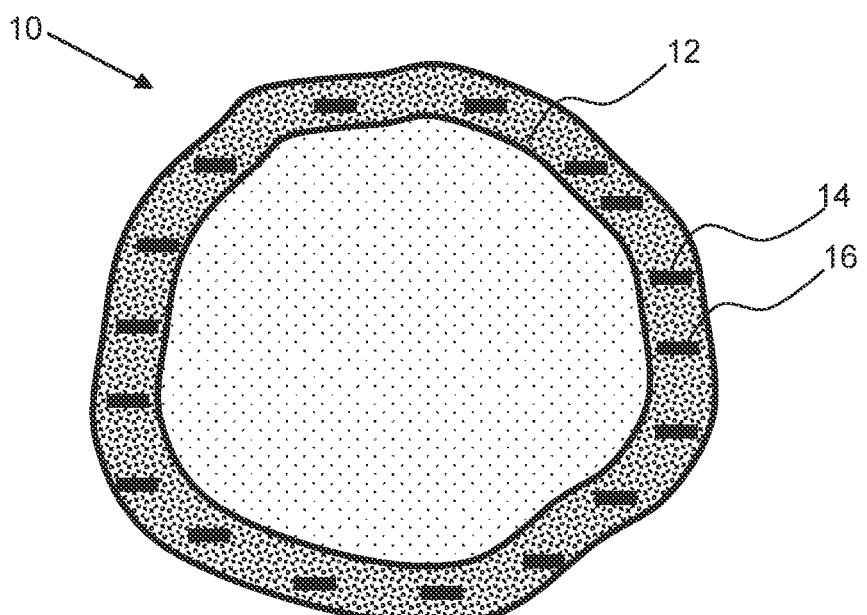
FIG. 1 shows a pathogen cell having a cell wall with negative charges.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, a pathogen cell 10, such as a bacterium cell 12, has a cell wall 14 with negative charges 16.

Figure 2:
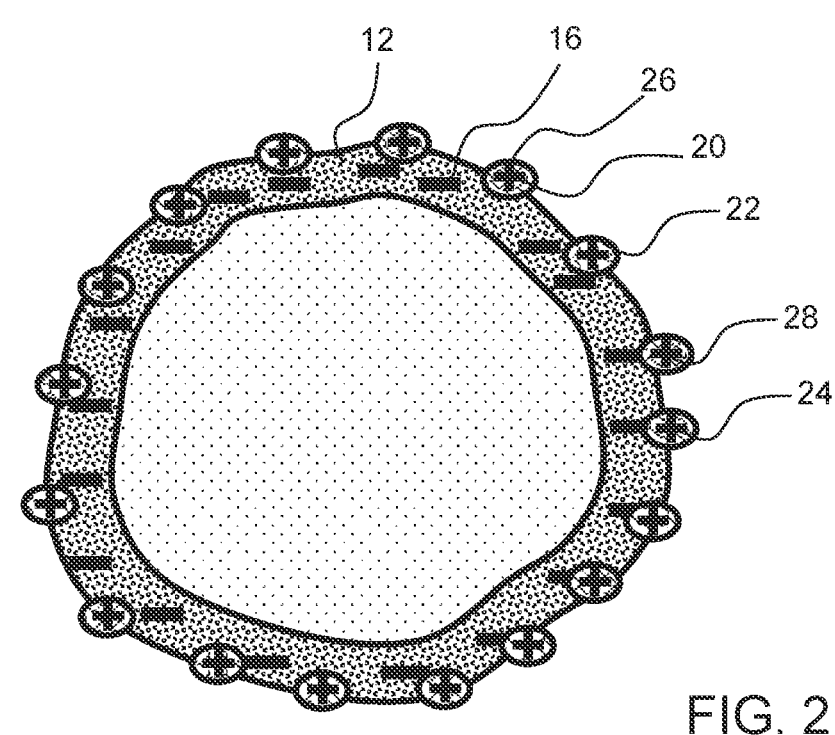
FIG. 2 shows the pathogen cell shown in FIG. 1, with biomarkers coupled to the cell wall via positive charge attraction to the negative charges in the pathogen cell wall.

As shown in FIG. 2, the pathogen cell shown in FIG. 1 has biomarkers 20, which are anionic biomarkers 22, coupled to the cell wall via a positive charge 26 of the anionic biomarker being attracted to the negative charges 16 in or on the pathogen cell wall 14. The anionic biomarker may also have a coupler portion 28, a portion that aids in coupling the biomarker to the pathogen cell. The anionic biomarker may have a magnetic material 24 associated therewith, such as being chemically or physical bound to the anionic biomarker. The magnetic material may be associated with the biomarker material prior to introduction into the body or may be introduced into the body subsequent to the biomarker being introduced.

Figures 3, 4:
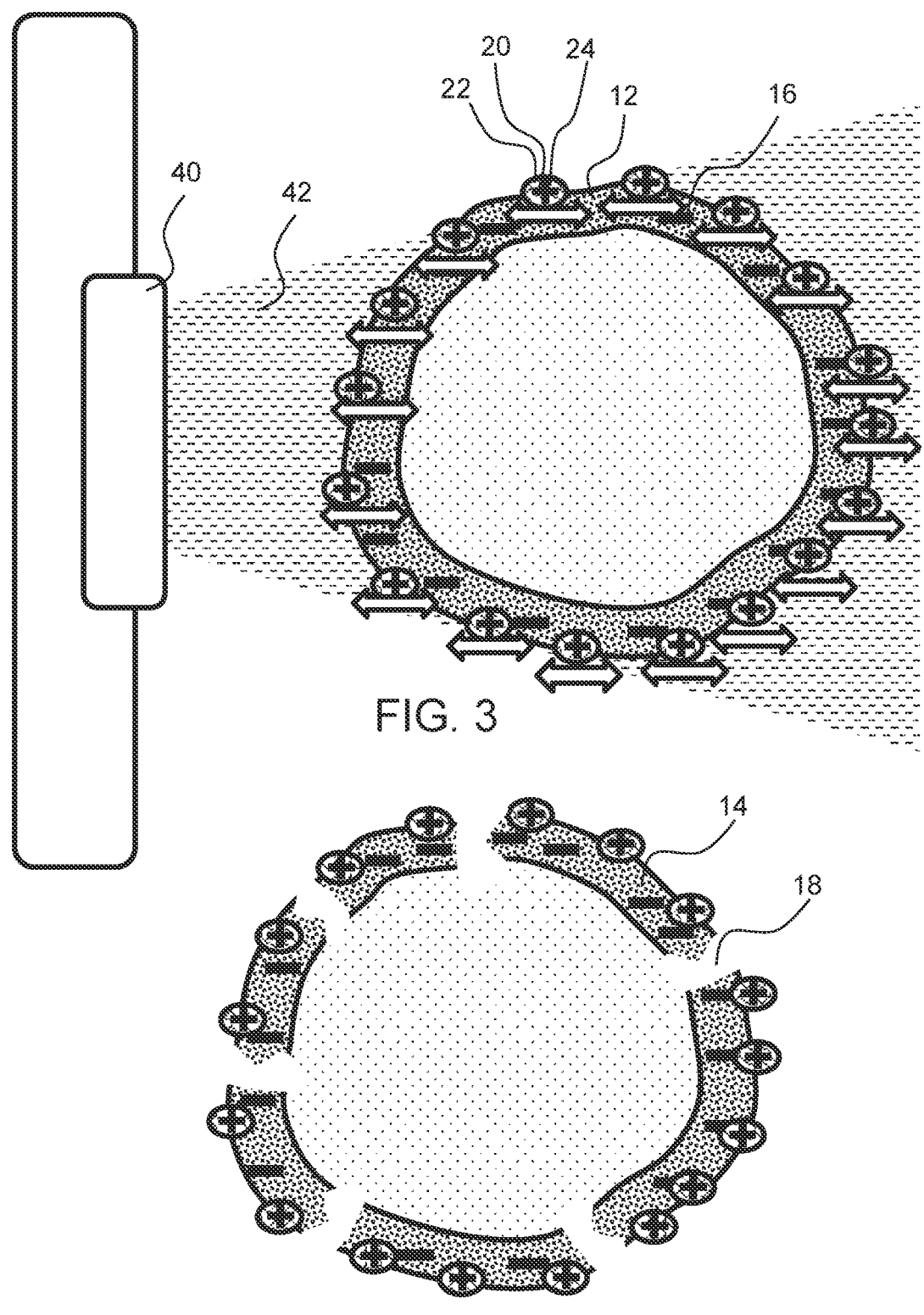
FIG. 3 shows the pathogen cell and coupled biomarkers exposed to an alternating magnetic field that causes the biomarkers to oscillate to damage the pathogen cell wall.
FIG. 4 shows the pathogen cell shown in FIG. 3 now destroyed due to the cell wall fractures caused by the oscillating biomarkers.

As shown in FIG. 3, the anionic biomarkers may have a magnetic material 24, that causes the biomarkers to move when exposed to a magnetic field 42. A magnetic field generator 40 may produce an alternating magnetic field that causes the biomarkers, or the magnetic material 24 thereof to oscillate when exposed to the alternating magnetic field and damage the pathogen cell wall 14. The frequency of the oscillation may be tuned to cause cell wall fractures 18 and destroy the pathogen cell.

As shown in FIG. 4, the pathogen cell wall 14 has a plurality of cell wall fractures 18 that effectively destroys the pathogen cell.

Figure 5:
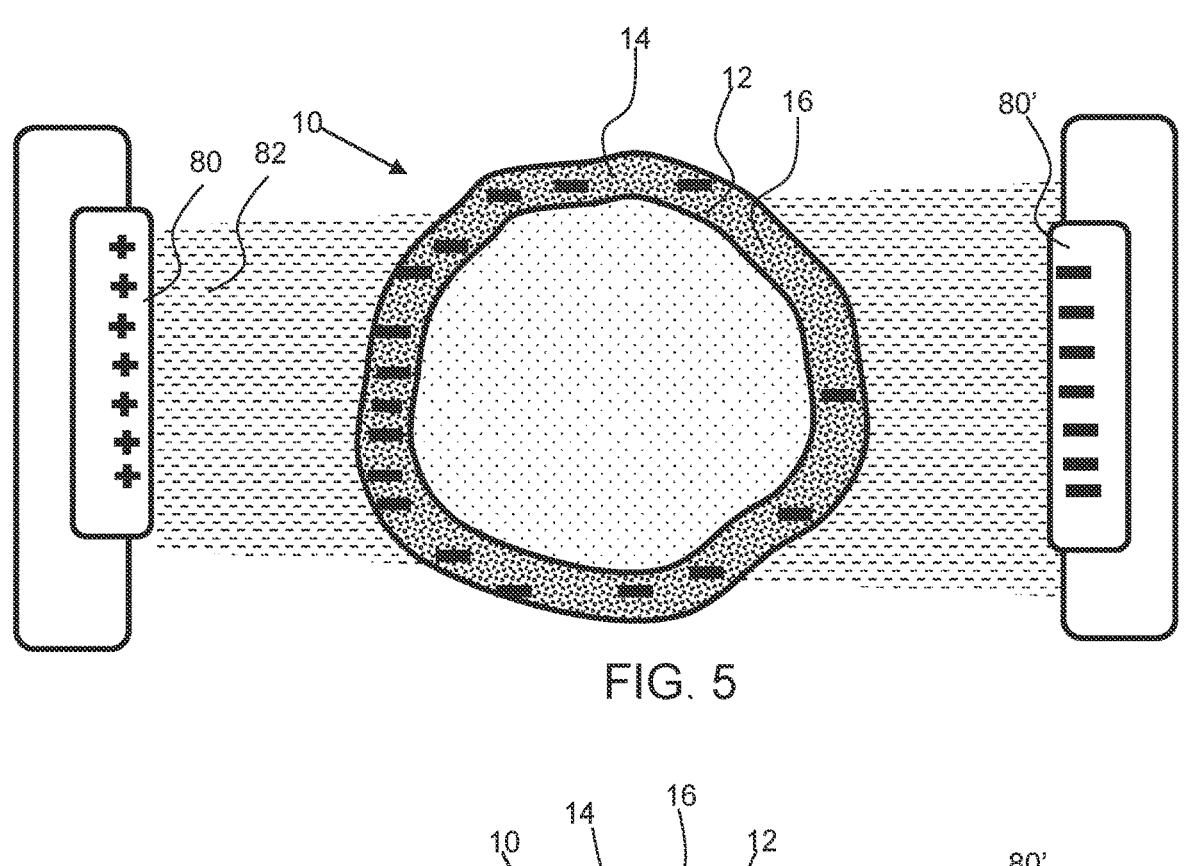
FIG. 5 shows a pathogen cell being exposed to an electric field.

As shown in FIG. 5, an electric field 82 may be produced by an electric field generator 80, which may include a charged plate or plates, that causes the pathogen cell to be polarized, wherein the charges are concentrated in alignment with the electric field. As shown, the negative charges of the pathogen cell 10 have concentrated on the side of the cell closest to the positive electrode.

Figure 6:
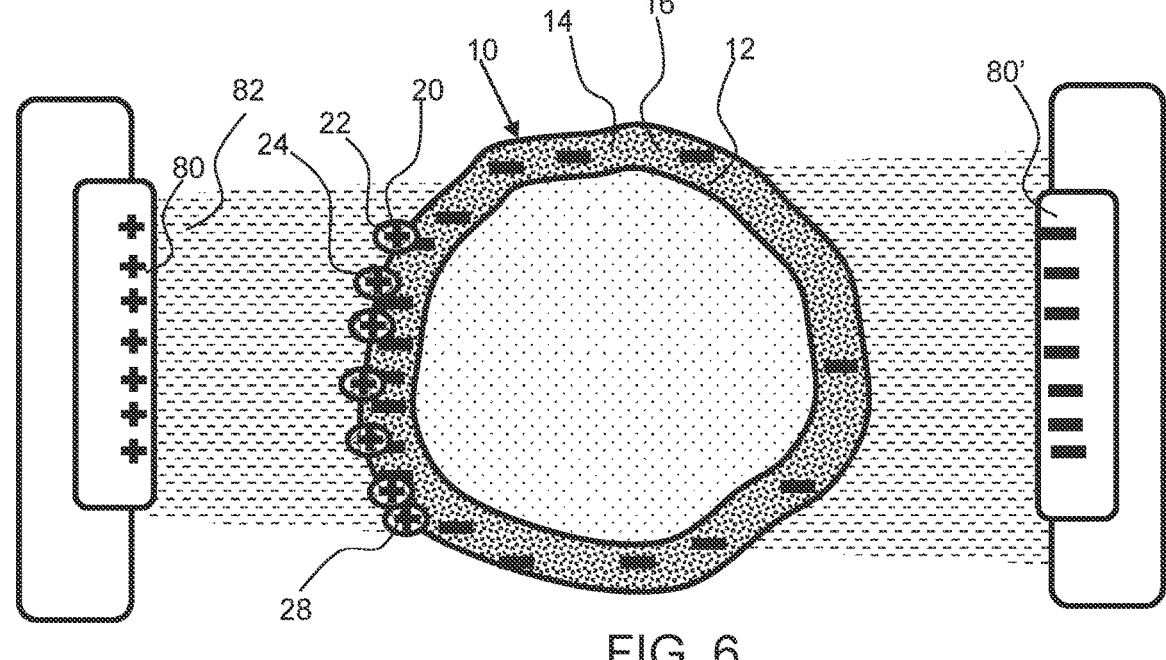
FIG. 6 shows a pathogen cell having anionic biomarkers coupled thereto and being exposed to an electric field.

As shown in FIG. 6, the anionic biomarkers 20 have associated and coupled with the pathogen cell 10 and are also concentrated as a result of the pathogen cell being polarized. Note that the electric field 82 may be turned off or may be an alternating electric field to enable the anionic biomarkers to couple with the cell, or move and align with the electric field, as shown. Also, the electric field may be used in combination with the magnetic field 42 as shown in FIG. 3. The magnetic field and electric fields may be operated in conjunction with each other to move the anionic biomarker and/or the magnetic material coupled thereto and damage the pathogen cell well 14.

Figure 7:
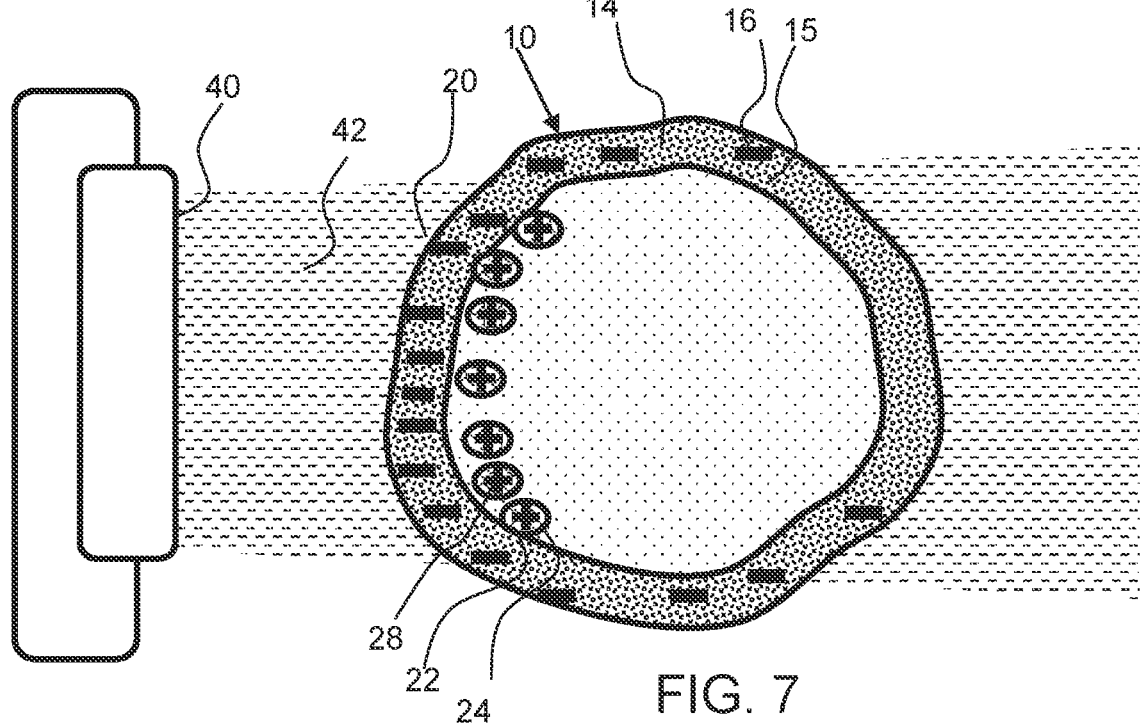
FIG. 7 shows a malignant cell having a biomarker coupled thereto and being exposed to magnetic field to destroy the malignant cell via movement of the magnetic material associated with the biomarker.

FIG. 7 shows a malignant cell 15 having a biomarker 20 coupled thereto and being exposed to magnetic field 42, via a magnetic field generator 40, such as a magnet, to destroy the malignant cell via movement of the magnetic material 24 associated with the biomarker.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A pathogen cell destruction method comprising:
a) providing an anionic biomarker;
b) providing a magnetic material that is coupled with the biomarker;
c) introducing the biomarker into an organism having a pathogen cell with a negative charge;
d) allowing the anionic biomarker to couple to the pathogen cell;
e) providing a magnetic field generator that produces a magnetic field;
f) directing the magnetic field to cause the magnetic material of the anionic biomarker to move and damage the pathogen cell and thereby destroy the pathogen cell;
g) providing an electric field generator; and
h) producing an electric field to polarize the pathogen cell;
wherein the anionic biomarker further comprises a coupler portion that is configured to couple with the pathogen cell
wherein the magnetic field generator generates an alternating magnetic field; and wherein the magnetic material is physically bound to the anionic biomarker.

2. The pathogen cell destruction method of claim 1, wherein the magnetic material coupled with the anionic biomarker comprises iron.

3. The pathogen cell destruction method of claim 2, wherein the magnetic material coupled with the anionic biomarker comprises nanoparticles of said iron.

4. The pathogen cell destruction method of claim 1, wherein the anionic biomarker comprises a ferromagnetic metal.

5. The pathogen cell destruction method of claim 4, wherein the anionic biomarker comprises nanoparticles of said ferromagnetic metal.

6. The pathogen cell destruction method of claim 1, wherein the magnetic material is chemically bound to the anionic biomarker.

7. The pathogen cell destruction method of claim 1, wherein the electric field is generated before the anionic biomarker is coupled to the pathogen cell.

8. The pathogen cell destruction method of claim 1, wherein the electric field is generated before the magnetic field is produced.

9. The pathogen cell destruction method of claim 1, wherein the electric field is generated simultaneously with the magnetic field.

10. The pathogen cell destruction method of claim 6, wherein the pathogen cell is an oncological cell.

11. The pathogen cell destruction method of claim 1, wherein the pathogen cell is an oncological cell.

* * * * *